US005621004A

United States Patent [19]
Dunn et al.

[11] Patent Number: 5,621,004
[45] Date of Patent: Apr. 15, 1997

[54] METHOD FOR TREATING EMESIS

[75] Inventors: Robert W. Dunn, P.O. Box 894, Old Lyme, Conn. 06371; Robert L. Gregory, New Providence, N.J.

[73] Assignee: Robert W. Dunn, Old Lyme, Conn.

[21] Appl. No.: 253,467

[22] Filed: Jun. 3, 1994

[51] Int. Cl.$^6$ .......................... A61K 31/22; A61K 31/195
[52] U.S. Cl. .......................... 514/551; 514/565; 514/872
[58] Field of Search ................................. 514/551, 565, 514/872

[56] References Cited

U.S. PATENT DOCUMENTS

| 5,039,528 | 8/1991 | Olney | 424/451 |
| 5,246,970 | 9/1993 | Williamson et al. | 514/632 |
| 5,246,971 | 9/1993 | Williamson et al. | 514/634 |
| 5,286,739 | 2/1994 | Kilbourn et al. | 514/400 |

OTHER PUBLICATIONS

M.T. Price et al., *Society for Neuroscience Abstracts*, (161.4) (1990).

Anders Fink–Jenssen et al., *Neuroscience Letters*, vol. 137, pp. 173–177 (1992).

A.L. Jones et al, "Management of vomiting associated with cytotoxic therapy", *Brit. J. Hosp. Med.*, vol. 45, pp. 85–89 (Feb. 1991).

D.D. Rees et al, "Characterization of three inhibitors of endothelial nitric oxide synthase in vitro and in vivo", *Br. J. Pharmacol*, vol. 101, pp. 746–752 (1990).

P.K. Moore et al, "L–N$^G$–nitro arginine methyl ester exhibits antiociceptive activity in the mouse", *Br. J. Pharmacol*, vol. 102, pp. 198–202 (1991).

P.K. Moore et al, "7–Nitro indazole, an inhibitor of nitric oxide synthase, exhibits anti–nociceptive activity in the mouse without increasing blood pressure", *Br. J. Pharmacol*, vol. 108, pp. 296–297 (1993).

R.C. Babbedge et al, "Inhibition of rat cerebellar nitric oxide synthase by 7–nitro indazole and related substituted indazoles", *Br. J. Pharmacol*, vol. 110, pp. 225–228 (1993).

J. Lehmann, "Nitric Oxide", *DN&P* 5(10), pp. 611–614 (Dec. 1992).

S.K. Kallar, "New Modalities in Postoperative Nausea and Vomiting", *J. Clin. Anesth.*, vol. 4 (Suppl. 1), pp. 16S–19S (Sep./Oct. 1992).

C.J. Lowenstein et al, "Nitric Oxide, a Novel Biologic Messenger", *Cell*, vol. 70, pp. 705–707 (Sep. 4, 1992).

S.T. Meller et al, "Nitric oxide (NO) and nociceptive processing in the spinal cord", *Pain*, vol. 52, pp. 127–136 (1993).

P.L. Feldman et al, "The suprising life of Nitric Oxide", *C&EN*, pp. 26–38 (Dec. 20, 1993).

A.D. Medhurst et al, "Nitric oxide synthase inhibitors 7–and 6–nitroindazole relax smooth muscle to vitro", *Euro. J. Pharma.*, vol. 256, pp. R5–R6 (Mar. 1994).

M.F. Watcha et al, "Postoperative Nausea and Vomiting", *Anesthesiology*, vol. 77, No. 1, pp. 162–184 (Jul. 1992).

P.L. Feldman, "N$^G$–Allyl and N$^G$–Cyclopropyl–L–arginine: Two Novel Inhibitors of Macrophage Nitric Oxide Synthase", *Chemtracts—Organic Chemistry*, 5:217–221 (Jul./Aug. 1992).

*Primary Examiner*—Marianne M. Cintins
*Assistant Examiner*—M. Moezie
*Attorney, Agent, or Firm*—Watov & Kipnes, P.C.

[57] ABSTRACT

A method of treating emesis in a warm blooded animal by administering an anti-emesis effective amount of a nitric oxide synthase inhibitor and compositions containing the same.

7 Claims, No Drawings

METHOD FOR TREATING EMESIS

The present invention is directed to a method of treating emesis in a warm-blooded animal by administering to said warm-blooded animal an anti-emesis effective amount of a nitric oxide synthase inhibitor.

BACKGROUND OF THE INVENTION

Emesis is the complex process in some warm-blooded animals, including humans, in which the stomach is evacuated through the esophagus and mouth due to strong muscular contractions in the abdomen. Commonly known as vomiting or retching, emesis is associated with nausea, malaise and general discomfort. The mechanism by which emesis is induced is complex. A detailed discussion of the process is disclosed in, for example, Mehernoor F. Watcha et al., "Postoperative Nausea and Vomiting", *Anesthesiology*, Vol. 67, pp. 162–184 (1992).

The biochemical basis of emesis stems from the presence of an emesis center within the brain. This center is located specifically in a region designated anatomically as the area postrema. This specialized area of the brain is distinguished from other regions of the central nervous system by the fact that it does not have a blood brain barrier to prevent substances circulating in the blood from freely entering therein.

Current work suggests that neurons in the area postrema serve as sensors of noxious substances circulating in the blood. Once these substances enter the area postrema and are sensed by the neurons as harmful, a message in the form of electrical impulses is triggered to evacuate the gastrointestinal tract. The transmission of the electrical impulses is generated when sufficient positive charge has been built up in the neurons to cause depolarization and a subsequent action potential. This action potential causes the release of a chemical neurotransmitter molecule from the pre-synaptic terminal into the synaptic cleft. The neurotransmitter molecule diffuses from one neuron through extracellular fluid, across the synapse, to a membrane receptor molecule of a post-synaptic neuron. Several chemical neurotransmitter systems involved in emesis have been identified based on the type of neurotransmitter molecule and include those based on glutamate, dopamine and serotonin.

Efforts at mediating the emetic process have focused on disrupting these neurotransmitter systems. For example, inhibitors of dopamine and serotonin have been used to treat emesis as disclosed in Alison L. Jones et al., "Management of Vomiting Associated With Cytotoxic Therapy", *Br. J. of Hosp. Med.*, Vol. 45, pp. 85–88 (February 1991). Glutamate receptor antagonists, such as kynurenic acid or 7-chlorokynurenate, have also been proposed as anti-emesis agents in John W. Olney, U.S. Pat. No. 5,039,528.

In the glutamate based neurotransmitter system, the presence of excess glutamate triggers an emesis response. Under these circumstances, excess calcium ions pass through a neuronal channel and upon entering the cell activate calmodulin. This substance activates nitric oxide synthase which in turn is responsible for converting L-arginine into citrulline and nitric oxide. Nitric oxide is believed to activate guanylate cyclase to produce cyclic GMP which may be directly involved in triggering the emetic process.

There are at least three distinct forms of nitric oxide synthase (NOS) found in the body. The first type is neuronal NOS found principally in the brain and in non-adrenergic, non-cholinergic (NANC) neurons in the gut. Endothelial NOS and inducible NOS (found in macrophages) are the second and third types. Endothelial NOS, found in the endothelial tissues, affects blood circulation by producing nitric oxide which acts as a vasodilator. Accordingly, endothelial NOS has been implicated in such conditions as hypertension, endotoxin shock (e.g. septic shock) and thrombosis.

Inducible NOS triggers the production of nitric oxide when the body is exposed to an endotoxin, and has been associated with such chronic ailments as ulcerative colitis and arthritis.

The production of nitric oxide can be inhibited by a class of compounds known as NOS inhibitors. For example, Interleukin-1 and lipopolysaccharides are known to inhibit the activity of macrophage NOS such as disclosed in Joseph R. Williamson et al., U.S. Pat. Nos. 5,245,970 and 5,246,971. Analogues of L-arginine including $N^G$-monomethyl-L-arginine (L-NMMA), N-iminoethyl-L-ornithine (L-NIO) and $N^G$-nitro-L-arginine methyl ester (L-NAME) have been shown to inhibit endothelial NOS. D. D. Rees et al., *Br. J. Pharmacol*, Vol. 101, pp. 746–752 (1990).

The present invention is premised on the discovery that compounds which effectively inhibit nitric oxide synthase, especially neuronal NOS, when administered in effective doses, can be employed as potent anti-emesis agents.

SUMMARY OF THE INVENTION

The present invention provides a method of treating emesis in a warm blooded animal comprising administering to said warm blooded animal an anti-emesis effective amount of a nitric oxide synthase inhibitor. In a preferred form of the invention, the nitric oxide synthase inhibitor is one which inhibits at least neuronal nitric oxide synthase in the conversion of L-arginine to citrulline and nitric oxide. In a preferred form of the invention, the nitric oxide synthase inhibitor substantially inhibits the activity of neuronal nitric oxide synthase and minimally inhibits the activity of endothelial and/or inducible nitric oxide synthases. The administration of a nitric oxide synthase inhibitor in accordance with the present invention minimizes or eliminates the production of nitric oxide and thus the production of cyclic GMP. As a result, the emetic process is attenuated.

DETAILED DESCRIPTION OF THE INVENTION

The present invention is directed to a method of treating emesis through the administration of a nitric oxide synthase inhibitor. The term "treating" as utilized herein is intended to mean both prophylactic and curative applications. The compounds of the invention can be administered after the onset of emesis, at the first appearance of symptoms indicating potential emesis.

Specific examples of the nitric oxide synthase inhibitors for use in the present invention include L-$N^G$-nitro-arginine methyl ester (L-NAME) and L-$N^G$-nitro-arginine (L-NOARG). The nitric oxide synthase inhibitors of the present invention may be administered to a warm-blooded animal in amounts of at least 0.0001 mg/kg of body weight of said animal, preferably from about 0.0001 to 10.0 mg/kg of body weight.

The nitric oxide synthase inhibitors of the present invention are typically combined with a pharmaceutically acceptable carrier which is selected depending on whether the inhibitor is water-soluble or water insoluble. Examples of suitable carriers include isotonic saline, distilled water, dilute hydrochloric acid, bicarbonates, dimethyl sulfoxide, mixtures of alcohols, such as ethanol and propylene glycol, and saline, and the like. For example, effective carriers include a mixture of 10% by volume of ethanol, 40% by volume of propylene glycol, and 50% by volume of saline as well as a mixture of 10% by volume (ethanol and emulphor), 60% by volume propylene glycol and 30% by volume of saline.

Compositions for parenteral administration contain from about 0.1% to about 50% by weight of the nitric oxide synthase inhibitors of the subject invention. The amount present will depend on the potency of the active ingredient and its solubility in the pharmaceutical vehicle. In general, the compositions contain sufficient active ingredient so that the practioner may titrate the dosage if desired and still be able to administer the maximum dosage in a parenteral container without giving the patient an unduly large amount of fluid. The nitric oxide synthase inhibitors may be combined with the carrier at room temperature, particularly when they are highly soluble in the carrier. For nitric oxide synthase inhibitors of lower solubility, it may be desirable to heat the carrier to temperatures below its boiling point to effect solution.

The composition containing the nitric oxide synthase inhibitor is administered parentally, preferably by intravenous injection. The composition of the present invention upon administration to a warm blooded animal, effectively prevents and alleviates emesis, particularly severe episodes which result from the application of chemotherapeutic agents, opiates or systemic anesthesic agents. An example of the advantageous breadth of anti-emesis activity of the nitric oxide synthase inhibitors of the present invention is their effectiveness against emesis induced by the administration of cisplatin. Few conventional anti-emesis agents have been show" to be effective against cisplatin-induced emesis.

EXAMPLE 1

Six naive male ferrets (castrated, descented; Triple F Farms) were individually cared for in a vivarium for one week prior to testing with regularly available supplies of food and water. Each ferret, weighing between 1 and 2 kilograms on the day of the test was allowed to acclimate to the laboratory environment for at least 30 minutes. Each ferret was anesthetized with 5% isoflurane-oxygen mixture delivered by a Fortec vaporizer for 2 to 5 minutes until the animals lost their righting reflex.

The test animals were maintained at this level of anesthesia and then injected intravenously with one ml/kg of a composition containing $N^G$-nitro-L-arginine methyl ester (L-NAME) in saline in the dosage amounts shown in Table 1. The injection was made into the cephalic vein of the dorsal aspect of the front paw. Thereafter, the anesthetic agent was withdrawn and 30 minutes later, morphine sulfate (0.3 mg/kg of body weight of the test animals) was administered subcutaneously into the nape of the neck. The animals were observed for emetic episodes which are defined as the oral expulsion of solids or liquids and retches which are rhythmic abdominal contractions with no expulsion of material. Observations were recorded for 30 minutes following morphine administration.

The mean and standard error of the mean (SEM) for emetic episodes was determined for each dose group and controls. The effect of the treatment is calculated as the percent protection of emetic episodes according to the following formula:

$$\frac{\text{Mean episodes of vehicle} - \text{mean episodes of inhibitor}}{\text{Mean episodes of vehicle}} \times 100 = \% \text{ protection}$$

The results are shown in Table 1.

TABLE 1

| Dose (mg/kg, iv) | Emetic Episodes (mean ± SEM) | % Protection of Emetic Episodes |
|---|---|---|
| 0 | 11.3 ± 1.3 | 0 |
| 0.0001 | 7.5 ± 2.5 | 34 |
| 0.001 | 6.3 ± 1.6 | 44 |
| 0.01 | 4.2 ± 0.8 | 63 |
| 0.1 | 5.2 ± 1.2 | 54 |
| 1.0 | 2.8 ± 0.4 | 75 |

As shown in Table 1, administration of just 0.0001 mg/kg of body weight of the nitric oxide synthase inhibitor resulted in a significant improvement in the protection of the test animals against emetic episodes induced by morphine sulfate. As the dose was increased to 1.0 mg/kg of body weight, the percentage protection increased to 75%.

EXAMPLE 2

The test described in Example 1 was repeated except that cisplatin (10 mg/kg of body weight) was used as the emesis inducing stimulus. Cisplatin, which is generally regarded as a more severe emetic than morphine sulfate, does not respond to treatment with most conventional anti-emesis agents.

Due to a comparatively slow onset of activity, cisplantin was administered intravenously 30 minutes prior to the administration of the nitric oxide synthase inhibitor (L-NAME). The anesthetic agent was administered for from 2 to 5 minutes during each injection. The test animals were observed for 60 minutes following administration of L-NAME. The results are shown in Table 2.

TABLE 2

| Dose (mg/kg, iv) | Emetic Episodes (mean ± SEM) | % Protection of Emetic Episodes |
| --- | --- | --- |
| 0 | 20.0 ± 4.5 | 0 |
| 0.001 | 11.3 ± 3.5 | 44 |
| 0.01 | 12.3 ± 5.2 | 39 |
| 0.1 | 9.3 ± 3.1 | 54 |
| 1.0 | 6.3 ± 2.2 | 69 |
| 10.0 | 4.3 ± 1.7 | 79 |

The results shown in Table 2 indicate that significant improvement in protection of the test animals against emetic episodes caused by cisplatin is obtained by employing the composition of the present invention.

EXAMPLE 3

The test described in Example 1 was repeated except that the nitric oxide synthase inhibitor was L-$N^G$-nitro-arginine in the dosage amounts set forth in Table 3. The results are shown in Table 3.

TABLE 3

| Dose (mg/kg, iv) | Emetic Episodes (mean ± SEM) | % Protection of Emetic Episodes |
| --- | --- | --- |
| 0 | 11.0 ± 1.4 | 0 |
| 0.01 | 9.3 ± 2.0 | 15 |
| 0.1 | 6.7 ± 2.0 | 41 |
| 1.0 | 5.5 ± 1.5 | 51 |
| 10.0 | 2.2 ± 0.9 | 81 |

As shown in Table 3, the administration of the composition of the present invention results in significant protection of the test animals against emetic episodes induced by morphine sulfate.

EXAMPLE 4

The test described in Example 2 was repeated except that the nitric oxide synthase inhibitor was L-$N^G$-nitro-arginine in the dosage amounts set forth in Table 4. The results are set forth in Table 4.

TABLE 4

| Dose (mg/kg, iv) | Emetic Episodes (mean ± SEM) | % Protection of Emetic Episodes |
| --- | --- | --- |
| 0 | 18.8 ± 3.8 | 0 |
| 0.001 | 12.7 ± 5.0 | 32 |
| 0.01 | 7.3 ± 1.0 | 61 |
| 0.1 | 5.0 ± 0.5 | 73 |
| 1.0 | 9.0 ± 2.2 | 52 |
| 10.0 | 3.0 ± 0.9 | 84 |

As shown in Table 4, the administration of the composition of the present invention results in significant protection of the test animals against emetic episodes induced by cisplantin.

EXAMPLE 5

The procedure described in Example 1 was repeated except that $N^G$-nitro-D-arginine methyl ester (D-NAME), a stereoisomer of L-NAME which is devoid of NOS inhibiting activity, was employed in the dosage amount set forth in Table 5. The results are shown in Table 5.

TABLE 5

| Dose (mg/kg, iv) | Emetic Episodes (mean ± SEM) | % Protection of Emetic Episodes |
| --- | --- | --- |
| 0 | 7.3 ± 1.0 | 0 |
| 1.0 | 7.0 ± 1.2 | 4 |

As shown in Table 5, the administration of D-NAME was ineffective and therefore did not provide protection for the test animals against emetic episodes induced by morphine sulfate.

EXAMPLE 6

The procedure described in Example 2 was repeated except that D-NAME in the dosage amount set forth in Table 6 was employed. The results are shown in Table 6.

TABLE 6

| Dose (mg/kg, iv) | Emetic Episodes (mean ± SEM) | % Protection of Emetic Episodes |
| --- | --- | --- |
| 0 | 17.5 ± 2.0 | 0 |
| 10.0 | 14.4 ± 1.3 | 18 |

As shown in Table 6, the administration of D-NAME was ineffective and therefore did not provide protection for the test animals against emetic episodes induced by cisplatin.

What is claimed:

1. A method of treating emesis in a warm blooded animal comprising administering to said warm blooded animal an anti-emesis effective amount of a nitric oxide synthase inhibitor.

2. A method in accordance with claim 1, wherein said nitric oxide synthase inhibitor inhibits the activity of at least neuronal nitric oxide synthase.

3. A method in accordance with claim 2, wherein said nitric oxide synthase inhibitor inhibits the activity of neuronal nitric oxide synthase to a greater extent than at least one of endothelial nitric oxide synthase and inducible nitric oxide synthase to thereby prevent the production of nitric oxide in an amount sufficient to cause emesis.

4. A method in accordance with claim 1, wherein the anti-emesis effective amount of the nitric oxide synthase inhibitor is at least 0.0001 mg/kg of body weight of said animal.

5. A method in accordance with claim 4, wherein the anti-emesis effective amount of the nitric oxide synthase inhibitor is from about 0.0001 to 10.0 mg/kg of body weight of said animal.

6. A method in accordance with claim 1, wherein the nitric oxide synthase inhibitor is selected from the group consisting of L-$N^G$-nitro-arginine methyl ester and L-$N^G$-nitro-arginine.

7. A method in accordance with claim 1 wherein the nitric oxide synthase inhibitor acts directly on nitric oxide synthase to inhibit production thereof.

* * * * *